United States Patent [19]

Feiring

[11] 4,220,608
[45] Sep. 2, 1980

[54] PREPARATION OF 3,3,3-TRIFLUOROPROPENE-1

[75] Inventor: Andrew E. Feiring, Wilmington, Del.

[73] Assignee: E. I. Du Pont de Nemours and Company, Wilmington, Del.

[21] Appl. No.: 45,959

[22] Filed: Jun. 6, 1979

[51] Int. Cl.$^2$ .............................................. C07C 19/08
[52] U.S. Cl. ................................ 260/653.3; 260/653.7
[58] Field of Search ........................... 260/653.3, 653.7

[56] References Cited

U.S. PATENT DOCUMENTS

| | | | |
|---|---|---|---|
| 2,549,580 | 4/1951 | Denison et al. ................... | 260/653.3 |
| 2,787,646 | 4/1957 | Haszeldine ........................ | 260/653.3 |
| 2,889,379 | 6/1959 | Ruh et al. ........................... | 260/653.5 |
| 3,739,036 | 6/1973 | Valicenti et al. ................. | 260/653.3 |
| 3,752,850 | 8/1973 | Scherer et al. ................... | 260/653.7 |
| 3,859,424 | 1/1975 | Scherer et al. ................... | 423/53 |
| 4,078,007 | 3/1978 | Ferstandig ....................... | 260/653.7 |

Primary Examiner—C. Davis

[57] ABSTRACT

Process for preparing 3,3,3-trifluoropropene-1 by contacting and reacting at least one of 1,1,1,3-tetrachloropropane, 1,1,3-trichloropropene-1 and 3,3,3-trichloropropene-1 and HF, under autogenous pressure, at 140°–250° C., in the presence of at least a catalytic amount of an organic monoamine, a salt of the monoamine or an alkylene diamine, said monoamine and salt being of the formula $R_3N.(R'X)_n$ wherein n is 0 or 1, X is an appropriate anion, each R and R' is selected independently from H, alkyl of 1–16 carbon atoms, cycloalkyl of 6–10 carbon atoms, aryl of 6–10 carbon atoms and alkylaryl of 6–10 carbon atoms, provided, however, when n is 0, no more than two of the R groups are H and when n is 1, no more than three of the R and R' groups are H, and provided, however, $R_3N$ taken jointly is piperidine, pyrrolidine, indoline, isoindoline, pyridine, quinoline or isoquinoline, each optionally substituted with 1–3 methyl groups, said alkylene diamine being of the formula $R''_2N(CH_2)_mNR''_2$ wherein m is 2–10 and each R'' is selected independently from H, alkyl of 1–4 carbon atoms and phenyl, provided, however, when m is 2, each R'' is selected independently from alkyl of 1–4 carbon atoms and phenyl.

14 Claims, No Drawings

PREPARATION OF 3,3,3-TRIFLUOROPROPENE-1

DESCRIPTION

Technical Field

This invention relates to the preparation of 3,3,3-trifluoropropene-1.

Background

Haszeldine, *J. Chem. Soc.*, 3371 (1953) discloses that a small amount of 3,3,3-trifluoropropene-1 is formed during the isomerization of 3,3,3-trichloropropene-1 to 1,1,3-trichloropropene-1 using HF at 0° C. U.S. Pat. No. 2,549,580 discloses the conversion of 1,1-dichloropropene-1 to 1,1,1-trifluoropropane, by means of HF at 120° C. and 800 psi pressure, with the trifluoropropane being photochemically chlorinated to 1,1,1-trifluoro-3-chloropropane which is dehydrochlorinated with alkali to 3,3,3-trifluoropropene-1. U.S. Pat. No. 4,078,007 discloses the conversion of 1,1,1,3-tetrachloropropane to 1,1,1-trifluoro-3-chloropropane, by means of HF and a mixture of antimony trihalide and antimony pentahalide, with the trifluorochloropropane being dehydrochlorinated with alkali to 3,3,3-trifluoropropene-1. U.S. Pat. Nos. 2,889,379; 3,752,850; and 3,859,424 disclose various high temperature vapor phase processes for preparing 3,3,3-trifluoropropene-1 and/or 1,1,1-trifluoro-3-chloropropane from 1,1,1,3-tetrachloropropane and HF using chromyl fluoride catalysts. U.S. Pat. No. 3,739,036 discloses the conversion of 1,1,1,3-tetrachloropropane to 3,3,3-trifluoropropene-1 by means of sodium fluoride at 400°–475° C. Henne et al., *J. Am. Chem. Soc.*, 73, 1042 (1951) disclose that 3,3,3-trifluoropropene-1 can be obtained in small yields from 1,1,1,3-tetrachloropropane using $SbF_3Cl_2$ at 0° C. U.S. Pat. No. 2,787,646 discloses the use of $SbF_3Cl_2$ and $SbF_3$ for converting the compound of the formula $CMZ_2CX=CXY$, for example, 3,3,3-trichloropropene-1 or 1,1,3-trichloropropene-1, to the compound of the formula $CF_3CX=CHY$, for example, 3,3,3-trifluoropropene-1. Olah et al., *Synthesis*, 779 (1973) and 652, 653, 654 and 896 (1974) disclose the use of stable polyhydrogen fluoride/pyridine (or a trialkylamine) reagents which can be used in a series of hydrogen fluoride reactions carried out at atmospheric pressure up to 50°, including the hydrofluorination of alkenes. The latter reaction is carried out in a solvent, such as tetrahydrofuran.

DISCLOSURE OF INVENTION

For further comprehension of the invention, and of the objects and advantages thereof, reference may be had to the following description and to the appended claims in which the various novel features of the invention are more particularly set forth.

The invention herein resides in the process for preparing 3,3,3-trifluoropropene-1 by contacting and reacting at least one of 1,1,1,3-tetrachloropropane, 1,1,3-trichloropropene-1 and 3,3,3-trichloropropene-1 and HF, under autogenous pressure, at 140°–250° C., in the presence of at least a catalytic amount of an organic monoamine, a salt of the monoamine or an alkylene diamine, said monoamine and salt being of the formula $R_3N \cdot (R'X)_n$ wherein n is 0 or 1, X is an appropriate anion, each R and R' is selected independently from H, alkyl of 1–16 carbon atoms, cycloalkyl of 6–10 carbon atoms, aryl of 6–10 carbon atoms and alkylaryl of 6–10 carbon atoms, provided, however, when n is 0, no more than two of the R groups are H and when n is 1, no more than three of the R and R' groups are H, and provided, however, $R_3N$ taken jointly is piperidine, pyrrolidine, indoline, isoindoline, pyridine, quinoline or isoquinoline, each optionally substituted with 1–3 methyl groups, said alkylene diamine being of the formula $R''_2N\text{-}(CH_2)_m NR''_2$ wherein m is 2–10 and each R'' is selected independently from H, alkyl of 1–4 carbon atoms and phenyl, provided, however, when m is 2, each R'' is selected independently from alkyl of 1–4 carbon atoms and phenyl.

The process involves the reaction $CCl_3CH_2CH_2Cl$
and/or

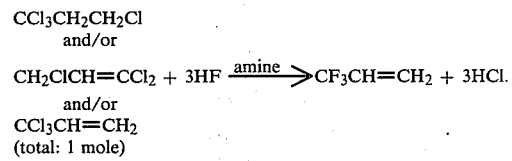

and/or
$CCl_3CH=CH_2$
(total: 1 mole)

At least 3 moles of HF are required to convert one mole of chlorinated starting material to trifluoropropene. An excess of HF, preferably two to ten times the stoichiometric requirement, is normally used in the reaction mixture to facilitate reaction of HF and the chlorinated starting material. More specifically, the molar ratio of HF to chlorinated starting material preferably is 6:1 to 30:1. The process of the invention can be operated in a batch or continuous mode, preferably the latter, under substantially anhydrous conditions. The reaction vessel is constructed from materials which are resistant to the action of hydrogen fluoride under the process conditions; examples of materials of construction include metal alloys such as Hastelloy C and plastic materials such as polytetrafluoroethylene.

In the batch mode of operation, reagents can be introduced in any order into the reaction vessel. Preferably, the chlorinated starting material and amine catalyst are introduced into the vessel which is then cooled and the required amount of HF is introduced. The vessel is closed and the contents are agitated by shaking or stirring at a reaction temperature of about 140°–250° C., preferably 150°–180° C., under autogenous pressure, until the reaction is substantially complete, whereupon the vessel is cooled to about room temperature. The gaseous contents of the vessel are vented through a scrubbing system which can contain aqueous caustic soda, soda lime or sodium fluoride pellets to remove acids, and then into a receiver which is cooled, for example, with dry ice and acetone, to facilitate collection of the product.

Alternatively, the reaction vessel can be equipped with a condenser and regulator valve so that the trifluoropropene and by-product HCl are removed as they are formed. Said regulator valve is set at 5 to 200 psi (34.5 to 1379 kPa), preferably 10 to 100 psi (69 to 689.5 kPa), above the autogenous pressure of the HF and amine mixture at the temperature of the reaction. The product stream can be scrubbed free of acids by passage through water, aqueous caustic soda, soda lime or sodium fluoride and then collected in a chilled receiver. The product can be analyzed by well-known techniques, such as gas-liquid chromatography (glpc), mass spectrometry (ms) or nuclear magnetic resonance spectroscopy (nmr).

The amines and amine salts, of the aforesaid formula, which are operable herein decrease the vapor pressure of the HF, thus enabling the desired reaction temperature of 140°-250° C. to be reached at reasonable pressures of HF. This feature of the invention process makes it possible to carry out the reaction without the use of special equipment which normally would be required to contain HF at such a temperature.

A further important feature of the invention process, especially in the preferred continuous operating mode, is the selective distillation of 3,3,3-trifluoropropene-1 and by-product HCl from the chlorocarbon/HF/amine reaction mixture, which drives the reaction towards completion and provides an easily-separable gaseous product mixture containing little or no HF.

Amines which are preferred in the practice of this invention include primary, secondary and tertiary amines and their salts, for example, trimethylamine, triethylamine, pyridine, quinoline, diisopropylamine, pyrrolidine, N,N,N', N'-tetramethylethylenediamine, n-nonylamine, 1,6-hexanediamine and hexadecycltrimethylammonium chloride. Trimethylamine, triethylamine, diisopropylamine, pyridine and quinoline are especially preferred. The amine can be introduced as the free amine or as its salt, such as the hydrochloride formed by adding hydrochloric acid to the amine.

The amount of the organic monoamine, salt of the monoamine or alkylene diamine employed in the process is such that it constitutes about 6 to 25 mole percent, preferably about 8 to 12 mole percent, of the combined molar amounts thereof and the HF.

The hydrogen fluoride and the aforesaid monoamine, amine salt and diamine are commercially available and can generally be used without further treatment or purification. Tetrachloropropane can be prepared according to the procedure of Asahara & Sato, *J. Chem. Soc. Japan, Ind. & Chem.*, 74, 703 (1971). The dehydrochlorination of 1,1,1,3-tetrachloropropane to 1,1,3- and 3,3,3-trichloropropene-1 is described by haszeldine, *loc. cit.*

Glpc analysis of the product can be carried out on a Hewlett Packard 5700A instrument using a 4 ft×⅛ in (1.22 m×3.175 mm) Porapak Q column with an oven temperature program of 60° to 200° C. at 4° C./min and a helium carrier gas flow rate of 40 ml/min. The product is identified by comparing its retention time to that of an authentic sample. The nmr spectrum is obtained in an appropriate solvent using tetramethylsilane and fluorotrichloromethane as the internal standards for proton and fluorine nmr, respectively.

In the following examples of specific embodiments of this invention process for preparing 3,3,3-trifluoropropene-1, percentages are by weight and temperatures are in °C. unless otherwise indicated. The heading on each example shows starting materials used in the example. As the term is used in Examples 4 to 14, "trichloropropenes" comprises a mixture of 1,1,3- and 3,3,3-trichloropropene-1.

EXAMPLE 1

1,1,1,3-Tetrachloropropane,

HF and Triethylamine

A 200 ml Hastelloy C pressure vessel was charged with 36.4 g (0.20 mole) of 1,1,1,3-tetrachloropropane and 30 g (0.30 mole) of triethylamine. The vessel was closed, cooled in dry ice and acetone, evacuated and charged with 70 g (3.5 mole) of HF. The vessel was agitated, with an inside temperature of 150°, for 6 hours. After cooling to room temperature the vessel was attached to a metal trap containing 300 g of soda lime, followed by a calibrated glass trap cooled in dry ice and acetone. The pressure vessel was vented slowly through the trap system until the internal pressure reached atmospheric pressure. The glass trap contained 9.0 ml of colorless liquid. The liquid was diluted to about 20 ml with a mixture of deuterochloroform, fluorotrichloromethane and tetramethylsilane. An aliquot of this solution, examined by nmr spectroscopy, showed a complex absorption at $\delta$5.4-6.2 in the proton spectrum and a doublet at $-67.37$ which collapsed to a singlet on proton decoupling in the fluorine spectrum, thereby identifying the product as 3,3,3-trifluoropropene-1.

EXAMPLE 2

1,1,1,3-Tetrachloropropane,

HF and Pyridine

The procedure of Example 1 was repeated, using 30 g of pyridine in place of the triethylamine, and gave 8.0 ml of 3,3,3-trifluoropropene-1.

EXAMPLE 3

1,1,3- and 3,3,3-Trichloropropene-1,

HF and Pyridine

An 80 ml Hastelloy C pressure vessel was charged with 17.6 g (0.12 mole) of mixed 1,1,3- and 3,3,3-trichloropropene-1 and 14.4 g (0.18 mole) of pyridine. The vessel was closed, cooled in dry ice and acetone, evacuated and charged with 32 g (1.6 moles) of HF. The vessel was agitated, with an inside temperature of 150°, for 6 hours. After cooling to room temperature the vessel contents were transferred to an evacuated stainless steel cylinder. The cylinder was vented through a tared polychlorotrifluoroethylene trap which was cooled in liquid nitrogen, giving 11.8 g of material. This material was distilled onto 5 g of sodium fluoride and 1 ml of pyridine to remove traces of HF and then distilled back into the tared trap, giving 9.3 g (81%) of 3,3,3-trifluoropropene-1, identified by its proton ($\delta$5.6-6.1) and fluorine ($-67.32$) nmr spectra.

EXAMPLE 4

1,1,3- and 3,3,3-Trichloropropene-1,

HF and Quinoline

A 100 ml Hastelloy C pressure vessel was charged with 14.55 g (0.10 mole) of trichloropropenes and 19.37 g (0.15 mole) of quinoline. The vessel was cooled in dry ice and acetone, evacuated and charged with 30 g (1.5 moles) of HF. The mixture was agitated for 6 hours, with an internal temperature of 150°. After cooling to room temperature the vessel was vented through a scrubber containing 45% aqueous potassium hydroxide, a drying tube containing anhydrous calcium sulfate and a glass trap cooled in a dry ice and acetone bath. The product which collected in the trap was transferred to a tared stainless steel cylinder, giving 3.8 g of 3,3,3-trifluoropropene-1, identified by gas chromatography.

EXAMPLE 5

1,1,3- and 3,3,3-Trichloropropene-1,

HF and n-Butylamine

The procedure of Example 4 was repeated, using 11 (0.15 mole) of n-butylamine in place of quinoline, and gave 3.3 g of 3,3,3-trifluoropropene-1.

EXAMPLE 6

1,1,3- and 3,3,3-Trichloropropene-1,

HF and Diisopropylamine

The procedure of Example 4 was repeated, using 15.2 g (0.15 mole) of diisopropylamine in place of quinoline, and gave 4.6 g of 3,3,3-trifluoropropene-1.

EXAMPLE 7

1,1,3- and 3,3,3-Trichloropropene-1,

HF and N,N,N',N'-Tetramethylethylenediamine

The procedure of Example 4 was repeated, using 17.4 g (0.15 mole) of N,N,N',N'-tetramethylethylenediamine in place of quinoline, and gave 2.96 g of 3,3,3-trifluoropropene-1.

EXAMPLE 8

1,1,3- and 3,3,3-Trichloropropene-1,

HF and N,N-Dimethylaniline

The procedure of Example 4 was repeated, using 18.2 g (0.15 mole) of N,N-dimethylaniline in place of quinoline, and gave 4.9 g of 3,3,3-trifluoropropene-1.

EXAMPLE 9

1,1,3- and 3,3,3-Trichloropropene-1,

HF and Piperidine

The procedure of Example 4 was repeated, using 12.8 g (0.15 mole) of piperidine in place of quinoline, and gave 1.5 g of 3,3,3-trifluoropropene-1.

EXAMPLE 10

1,1,3- and 3,3,3-Trichloropropene-1,

HF and n-Nonylamine

The procedure of Example 4 was repeated, using 20.3 g (0.14 mole) of n-nonylamine, 13.7 g (0.094 mole) of trichloropropenes and 30 g (1.5 moles) of HF, and gave 1.32 g of 3,3,3-trifluoropropene-1.

EXAMPLE 11

1,1,3- and 3,3,3-Trichloropropene-1,

HF and Triethylamine Hydrochloride

The procedure of Example 4 was repeated, using 11.2 g (0.081 mole) of triethylamine hydrochloride, 7.78 g (0.053 mole) of trichloropropenes and 17.0 g (0.85 mole) of HF, and gave 1.86 g of 3,3,3-trifluoropropene-1.

EXAMPLE 12

1,1,3- and 3,3,3-Trichloropropene-1,

HF and Hexadecyltrimethylammonium Chloride

The procedure of Example 4 was repeated, using 21.5 g (0.067 mole) of hexadecyltrimethylammonium chloride, 7.58 g (0.052 mole) of trichloropropenes and 16 g (0.80 mole) of HF, and gave 1.37 g of 3,3,3-trifluoropropene-1.

EXAMPLE 13

1,1,3- and 3,3,3-Trichloropropene-1,

HF and Trimethylamine

A 5 gallon (18.925 liter) Hastelloy C stirred autoclave was equipped with a water cooled condenser and lines for adding HF, trimethylamine and trichloropropenes. The condenser was equipped with a Grove valve leading to two 1-liter flasks filled with 20% aqueous potassium hydroxide, followed by a drying tube containing anhydrous calcium sulfate and a 1-liter stainless steel cylinder cooled in dry ice and acetone.

The reaction vessel autoclave was charged with 110 g (1.86 moles) of trimethylamine and 320 g (16 moles) of HF. This mixture was heated to 167°, giving an autogenous pressure of 130 psi (896.3 kPa). The Grove valve was set to release at 225 psi (1551.3 kPa). Over the course of 4 hours 436.5 g (3.0 moles) of trichloropropenes, 250 g (14 moles) of HF and 56 g (0.95 mole) of trimethylamine were added to the autoclave which operated at a temperature of 165°–175° and a pressure of 228 psi (1572.0 kPa). On recovery the stainless steel cylinder contained 178 g of material which analyzed as substantially pure 3,3,3-trifluoropropene-1 by glpc.

The combined aqueous scrubbing solutions were analyzed by titration for the presence of chloride and fluoride ions. Found: Cl, 6.00%, 6.00%; F, 0.08, 0.09 equiv/liter. The analyses showed that the by-product HCl is selectively distilled from the fluorinating mixture.

EXAMPLE 14

1,1,3- and 3,3,3-Trichloropropene-1,

HF and 1,6-Hexanediamine

The procedure of Example 4 was repeated, using 17.4 g (0.15 mole) of 1,6-hexanediamine in place of quinoline, and gave 1.57 g of 3,3,3-trifluoropropene-1.

BEST MODE FOR CARRYING OUT THE INVENTION

The best mode for carrying out the invention is illustrated by Example 13.

INDUSTRIAL APPLICABILITY

The process of this invention can be employed to produce 3,3,3-trifluoropropene-1 which is useful in the manufacture of chemically resistant polymers and which can be silylated to a fluorosilicone, for example, a 3,3,3-trifluoropropylmethylpolysiloxane lubricant. Other known uses of 3,3,3-trifluoropropene-1 include usage as an aerosol propellant and as a refrigerant.

I claim:

1. Process for preparing 3,3,3-trifluoropropene-1 by contacting and reacting at least one of 1,1,1,3-tetrachloropropane, 1,1,3-trichloropropene-1 and 3,3,3-trichloropropene-1 and HF, under autogeneous pressure, at 140°–250° C., in the presence of at least a catalytic amount of an organic monoamine, a salt of the monoamine or an alkylene diamine, said monoamine and salt being of the formula $R_3N \cdot (R'X)_n$ wherein n is 0 or 1, X is an appropriate anion, each R and R' is selected independently from H, alkyl of 1–16 carbon atoms, cycloalkyl of 6–10 carbon atoms, aryl of 6–10 carbon atoms and alkylaryl of 6–10 carbon atoms, provided, however, when n is 0, no more than two of the R groups are H and when n is 1, no more than three of the R and R' groups are H, and provided, however, $R_3N$ taken jointly is piperidine, pyrrolidine, indoline, isoindoline, pyridine, quinoline or isoquinoline, each optionally substituted with 1–3 methyl groups, said alkylene diamine being of the formula $R''_2-CH_2)_mNR''_2$ wherein m is 2–10 and each $R''$ is selected independently from H, alkyl of 1–4 carbon atoms and phenyl, provided, however, when m is 2, each R" is selected independently from alkyl of 1-4 carbon atoms and phenyl.

2. Process of claim 1 wherein the amount of organic monoamine, salt of the monoamine or alkylene diamine is about 6 to 25 mole percent, based on the combined molar amounts thereof and the HF.

3. Process of claim 2 wherein the amount of organic monoamine, salt of the monoamine or alkylene diamine is about 8 to 12 mole percent, based on the combined molar amounts thereof and the HF.

4. Process of claim 2 wherein an organic monoamine is employed.

5. Process of claim 4 wherein the monoamine is trimethylamine.

6. Process of claim 4 wherein the monoamine is pyridine.

7. Process of claim 2 wherein a salt of the monoamine is employed.

8. Process of claim 7 wherein the salt is hexadecyltrimethylammonium chloride.

9. Process of claim 2 wherein an alkylene diamine is employed.

10. Process of claim 9 wherein the diamine is N,N,N',N'-tetramethylethylenediamine.

11. Process of claim 1 wherein the reaction is carried out continuously.

12. Process of claim 11 wherein HCl and 3,3,3-trifluoropropene-1 are selectively distilled from the reaction mixture.

13. Process of claim 1 wherein the molar ratio of HF to chlorinated starting material in the reaction mixture is in excess of 3:1.

14. Process of claim 13 wherein the molar ratio is 6:1 to 30:1.

* * * * *